United States Patent [19]

Honma et al.

[11] Patent Number: 5,608,057
[45] Date of Patent: Mar. 4, 1997

[54] N-(ALPHA-ACYLOXYETHYL) COMPOUND AND METHOD FOR THE PREPARATION THEREOF

[75] Inventors: Yoshihiro Honma, Osaka-fu; Shozo Tanaka, Nara-ken; Mitsuyoshi Oshima, Niigata-ken; Soji Tanioka, Tokyo; Fumiaki Kawamoto, Osaka-fu, all of Japan

[73] Assignee: Shin-Etsu Vinyl Acetate Co., Ltd., Japan

[21] Appl. No.: 518,303

[22] Filed: Aug. 23, 1995

[30] Foreign Application Priority Data

Aug. 31, 1994 [JP] Japan ................................ 6-206345

[51] Int. Cl.$^6$ .................. C07C 233/31; C07D 223/10
[52] U.S. Cl. .................. 540/451; 540/454; 540/485; 540/488; 544/97; 546/243; 548/229; 548/547; 560/250; 528/323
[58] Field of Search .................. 540/451, 454, 540/485, 488; 544/97; 546/243; 548/229, 547; 560/250

[56] References Cited

FOREIGN PATENT DOCUMENTS

| | | |
|---|---|---|
| 0350666A2 | 1/1990 | European Pat. Off. . |
| 0608690A1 | 8/1994 | European Pat. Off. . |
| 1421336 | 11/1965 | France . |
| 1232946 | 1/1967 | Germany . |

OTHER PUBLICATIONS

*Chemical Abstracts*, 77(8), 22, abstract No. 49091j (Aug. 1972) (abstract of JP-A-07 208 302).

*Chemical Astracts*, 77(8), 22, abstract no. 49092k (Aug. 1972) (abstract of JP-A-07 208 303).

*Primary Examiner*—Robert T. Bond
*Attorney, Agent, or Firm*—Wenderoth, Lind & Ponack

[57] ABSTRACT

Proposed are an N-(α-acyloxyethyl) compound, e.g., (N-(α-acetoxyethyl)-2-pyrrolidone, which is a novel compound and can be converted into an industrially very important N-vinyl compound, e.g., N-vinyl-2-pyrrolidone, by a thermal decomposition reaction under relatively mild conditions as well as a method for the preparation of such an N-(α-acyloxyethyl) compound. The N-(α-acyloxyethyl) compound can be synthesized in a high yield by the addition reaction of an NH group-containing compound, e.g., 2-pyrrolidone, with a vinyl carboxylate, e.g., vinyl acetate, in the presence of an alkaline compound such as alkali metal hydroxides.

13 Claims, No Drawings

N-(ALPHA-ACYLOXYETHYL) COMPOUND AND METHOD FOR THE PREPARATION THEREOF

BACKGROUND OF THE INVENTION

The present invention relates to an N-(α-acyloxyethyl) compound, which belongs to a class of novel organic compounds not known in the prior art nor described in any literatures, and a simple and efficient method for the preparation thereof. The present invention has been completed on the basis of an unexpected discovery obtained in the course of the investigations undertaken by the inventors with an object to develop an efficient method for the preparation of N-vinyl compounds having usefulness as a reactive monomeric compound for the preparation of special polymeric compounds.

As is known, N-vinyl compounds in general have good polymerizability and high reactivity so that they are widely used as a class of industrially very important reactive monomers in the preparation of various kinds of specialty polymers and as an ingredient in ultraviolet-curable resin compositions.

For example, N-vinyl-2-pyrrolidone is used as a starting monomer in the preparation of polyvinyl pyrrolidones as a typical water-soluble polymer or as an ingredient in an ultraviolet-curable resin composition. Further, various kinds of N-vinyl amide compounds are now highlighted and under extensive investigations as a starting monomer for the preparation of a polymer to be useful as a cationic polymeric flocculant, for example, in the process of sewage disposal.

Various methods have been proposed heretofore for the preparation of these N-vinyl compounds. Taking N-vinyl-2-pyrrolidone mentioned above as an example, known methods for the preparation thereof include: (1) a method in which acetylene and 2-pyrrolidone are reacted under high pressure or in the presence of an alkali as a catalyst as disclosed in U.S. Pat. No. 2,806,847 and French Patent 1,340,350; (2) a method in which a vinyl ether or a vinyl carboxylate and 2-pyrrolidone are reacted in the presence of a mercury salt or a palladium compound as a catalyst as disclosed in Japanese Patent Publications 38-4882, 47-8302, 47-8303, 47-2083 and 47-2001; (3) a method in which N-(α-hydroxyethyl) pyrrolidone or an N-(α-alkoxyethyl) pyrrolidone is subjected to thermal decomposition as disclosed in French Patents 1,534,369 and 1,421,336; (4) a method in which N-(β-hydroxyethyl) pyrrolidone or N-(β-acetoxyethyl) pyrrolidone is subjected to thermal decomposition as disclosed in Japanese Patent Publication 48-44251 and USSR Patent 125,507; and so on.

Among the above described prior art methods, the first method has already been rendered to practice as an industrial process although this method is never so advantageous because the investment for the plant construction is high as a consequence of the high-pressure reaction along with a risk due to eventual explosion. The other prior art methods are also industrially not practicable because the yield of the desired products cannot be high enough unless the reaction is conducted under very severe reaction conditions if not to mention the expensiveness of some of the starting materials and the catalyst compounds.

In view of the above described problems and disadvantages in the prior art methods for the preparation of an N-vinyl compound, the inventors have conducted extensive investigations to develop a simple and efficient method for the synthetic preparation of the compound by conducting experiments through a widely different routes starting from a variety of known compounds as well as some novel compounds which are not known in the prior art but supposedly could be a promising intermediate material for the synthesis of an N-vinyl compound.

SUMMARY OF THE INVENTION

The present invention accordingly has a primary object to propose an organic compound which can be a precursor in the preparation of an N-vinyl compound. The present invention has a further object to provide an N-(α-acyloxyethyl) compound which is a novel compound not known in the prior art but can meet the above mentioned primary object of the invention as well as to provide an efficient method for the synthetic preparation of the N-(α-acyloxyethyl) compound.

Thus, the N-(α-acyloxyethyl) compound provided by the invention is a compound represented by either one of the general formulas

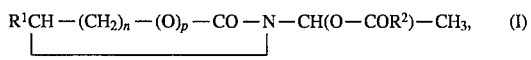

and

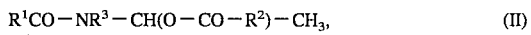

in which $R^1$ and $R^2$ are, each independently from the other, a hydrogen atom or a monovalent hydrocarbon group, $R^3$ is a monovalent hydrocarbon group, the subscript p is 0 or 1 and the subscript n is a positive integer not exceeding 10.

The above defined N-(α-acyloxyethyl) compound represented by the general formula (I) can be prepared by a method in which an NH group-containing compound represented by the general formula

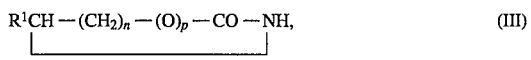

and a vinyl carboxylate represented by the general formula

in which each symbol has the same meaning as defined above, are mixed together with admixture of an alkaline compound as a catalyst to effect the addition reaction between the NH group-containing compound and the vinyl carboxylate.

Similarly, the N-(α-acyloxyethyl) compound represented by the general formula (II) can be prepared by a method in which an NH group-containing compound represented by the general formula

and a vinyl carboxylate represented by the general formula

in which each symbol has the same meaning as defined above, are mixed together with admixture of an alkaline compound as a catalyst to effect the addition reaction between the NH group-containing compound and the vinyl carboxylate.

DETAILED DESCRIPTION OF THE PREFERRED EMBODIMENTS

The N-(α-acyloxyethyl) compound provided by the invention, which is a novel compound not known in the prior art nor reported in any literatures, is represented by the above given general formula (I) or (II), in which $R^1$ and $R^2$ are, each independently from the other, a hydrogen atom or a monovalent hydrocarbon group, $R^3$ is a monovalent hydrocarbon group, the subscript p is 0 or 1 and the subscript n is a positive integer not exceeding 10.

The monovalent hydrocarbon group denoted by $R^1$, $R^2$ or $R^3$ is exemplified by aliphatic hydrocarbon groups such as methyl, ethyl, propyl, n-butyl and tert-butyl groups and aromatic hydrocarbon groups such as phenyl and tolyl groups.

The above defined novel N-(α-acyloxyethyl) compound can be synthesized by the addition reaction of a vinyl carboxylate of the general formula $R^2$—CO—O—CH=CH$_2$, in which $R^2$ has the meaning as defined above, to an NH group-containing compound represented by the general formula (III) or (V), respectively, in the presence of an alkaline compound as a catalyst according to the reaction equation

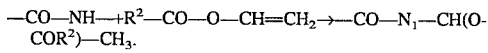

—CO—NH—+R$^2$—CO—O—CH=CH$_2$→—CO—N$_1$—CH(O-COR$^2$)—CH$_3$.

The starting NH group-containing compound is selected depending on the desired N-(α-acyloxyethyl) compound. When the desired N-(α-acyloxyethyl) compound is that expressed by the general formula (I) having a cyclic structure, the starting NH group-containing compound also should have a corresponding cyclic structure as represented by the general formula (III) given above, in which each symbol has the same meaning as defined above. Examples of the NH group-containing compound represented by the general formula (III) and suitable as the starting material of the N-(α-acyloxyethyl) compound represented by the general formula (I) include β-propiolactam, 2-pyrrolidone, δ-valerolactam, γ-valerolactam, 2-piperidone, ε-caprolactam, 2-azacyclononanone, 2-azacyclodecanone and laurolactam, for which the subscript p in the general formula (III) is zero, as well as 2-oxazolidinone and 5-methyl-2-oxazolidinone, for which the subscript p is 1. When the desired N-(α-acyloxyethyl) compound is that expressed by the general formula (II) having no cyclic structure, the starting NH group-containing compound is selected from the amide compounds represented by the general formula (V) given above. Examples of the NH group-containing compound represented by the general formula (V) and suitable as the starting material of the N-(α-acyloxyethyl) compound represented by the general formula (II) include N-methyl acetamide, N-ethyl acetamide and acetanilide.

The vinyl carboxylate as the other reactant in the addition reaction with the NH group-containing compound described above is selected depending on the desired $R^2$ group. Some of the examples of the vinyl carboxylate include vinyl acetate, vinyl propionate, vinyl butyrate, vinyl pivalate and vinyl benzoate.

The alkaline compound to promote the addition reaction between the above described reactants includes alkali and alkaline earth elements such as lithium, sodium, potassium, rubidium, cesium, magnesium, calcium and barium in the metallic form or in the form of a compound such as hydroxides, carbonates, hydrogen-carbonates, hydrogen-phosphates, acetates, alcoholates and the like, of which alkali metal hydroxides are preferable and potassium hydroxide and cesium hydroxide are more preferable.

In conducting the addition reaction between the above described reactants, the reactant compounds described above are mixed together with admixture of the alkaline compound so that the addition reaction proceeds even at room temperature to form the desired product. The amount of the vinyl carboxylate to be mixed with the NH group-containing compound is stoichiometrically equimolar to the NH group-containing compound as is understood from the above given reaction equation although the exact amount should be selected by taking into consideration various factors. For example, the amount of the vinyl carboxylate can be increased up to twice of the equimolar amount when partial decomposition of the vinyl carboxylate takes place during the reaction or when the product compound has a relatively high viscosity or high melting point.

The amount of the alkaline compound added to the mixture of the reactants is, though not particularly limitative, in the range from 0.0001 to 0.2 mole per mole of the NH group-containing compound. The reaction temperature can be in the range from −60° C. to 60° C. or, preferably, from −30° C. to 30° C. When the temperature is too high, side reactions may proceed predominantly. The reaction is complete usually within 60 minutes though dependent on various factors.

Following is a description of a particular procedure for conducting the addition reaction of the reactants although the inventive method is never limited thereto.

In the first place, the alkaline compound, e.g., potassium hydroxide KOH, is added to the NH group-containing compound as one of the reactants and dissolved therein to form a reaction mixture, if necessary, by heating. A side reaction may take place between the NH group and potassium hydroxide to form an NK group-containing compound with formation of water as a by-product. It is optional according to need that the reaction mixture is diluted by the addition of a suitable organic solvent having no reactivity with the reactant compounds and the alkaline compound as well as with the product compound such as hexane, benzene, tetrahydrofuran, dioxane and the like. After removal of this by-product water, which is formed more or less when an alkali hydroxide is used as the catalyst, by distillation under reduced pressure, the reaction mixture is admixed with the vinyl carboxylate dropwise under control of the temperature of the :mixture so that the addition reaction proceeds to form the desired N-(α-acyloxyethyl) compound as the product. After completion of the reaction, the reaction mixture is subjected to distillation under reduced pressure to remove the low boiling-point materials such as the unreacted reactants, by-products and solvent and the residual portion of the reaction mixture is subjected to a procedure for the isolation of the product compound such as precision distillation under reduced pressure, liquid chromatography, recrystallization and the like.

In the following, descriptions are given for the synthetic procedure and characterization of the inventive N-(α-acyloxyethyl) compounds by way of examples followed by some application examples for the preparation of N-vinyl compounds by the thermal decomposition of the inventive N-(α-acyloxyethyl) compound under mild reaction conditions.

EXAMPLE 1

A reaction mixture was prepared by dissolving 0.45 g (0.003 mole) of cesium hydroxide in 85 g (1 mole) of 2-pyrrolidone under gentle warming followed by the removal of the by-product water by distillation under reduced pressure. After cooling of the mixture to room temperature, 103 g (1.2 moles) of vinyl acetate were added dropwise into the reaction mixture under agitation over a period of 15 minutes, during which the temperature of the reaction mixture was kept in the range from −20° C. to 10° C. by means of external cooling to remove the heat of reaction.

After completion of the dropwise addition of 2-pyrrolidone, the reaction mixture was subjected to distillation under reduced pressure to remove the low boiling-point materials followed by standing of the remaining reaction mixture to settle the insoluble cesium compound, from which the liquid product was separated and taken by decantation. The thus obtained product in an amount of 164 g was subjected to the $^1$H- and $^{13}$C-NMR analysis, gas chromatographic-mass spectrometric analysis and infrared absorption spectrophotometric analysis under the following analytical conditions and could be identified to be N-(α-acetoxyethyl)-2-pyrrolidone. The above mentioned yield of the product corresponds to 96% of the theoretical value.

NMR analysis:
  Apparatus: Model GSX 270 FT-NMR, Nippon Denshi Co.
  Solvent: heavy benzene (d$_6$)
  Reference for shift in $^1$H-NMR: 0.0 ppm (tetramethyl silane, external standard)
  Reference for shift in $^{13}$C-NMR: 128.0 ppm (solvent)
  Temperature: room temperature Gas chromatographic-mass spectrometric analysis:
  Apparatus: Model Hitachi M-80B, GC-MS
  Method: direct introduction method Infrared absorption spectrophotometric analysis:
  Apparatus: Fourier-transformation infrared spectrophotometer Model JIR-5500, Nippon Denshi Co.
  Method: KBr tablet method The results of these instrumental analyses were as follows.

| Position of carbon atom | NMR analysis: (δ, ppm) | |
|---|---|---|
| | $^1$H-NMR | $^{13}$C-NMR |
| 1 | 1.7 (s) | 20.0 |
| 2 | — | 168.3 |
| 3 | 6.2 (q) | 72.6 |
| 4 | 1.1 (d) | 17.0 |
| 5 | — | 173.8 |
| 6 | 2.0 (m) | 30.4 |
| 7 | 1.7 (m) | 17.1 |
| 4 | 3.1 (m) | 41.2 |

$$\underset{}{\overset{8\ \ 7\ \ 6\ \ 5}{CH_2CH_2CH_2CN}}\!\!-\!\!\underset{\underset{\underset{O}{\parallel}}{\overset{2\ 1}{OCCH_3}}}{\overset{3\ \ 4}{CHCH_3}}$$

GC-MS analysis:
  A peak for a quasi-molecular ion M+1 corresponding to a mass number of 172 was detected by the chemical ionization method with isobutane as the reaction gas so that the molecular weight of the sample compound was 171.

IR analysis:
  1740 cm$^{-1}$ (carbonyl group at the carbon atom of position 2)
  1703 cm$^{-1}$ (carbonyl group at the carbon atom of position 5)
  1220 cm$^{-1}$ (—C—O— linkage at the carbon atom of position 2)

EXAMPLE 2

The synthetic procedure was substantially the same as in Example 1 excepting replacement of 103 g (1.2 moles) of vinyl acetate with 114 g (1 mole) of vinyl n-butyrate to obtain 181 g of a product which could be identified to be N-(α-n-butyryloxyethyl)-2-pyrrolidone (91% yield of the theoretical value) from the results of the instrumental analyses shown below.

| Position of carbon atom | NMR analysis: (δ, ppm) | |
|---|---|---|
| | $^1$H-NMR | $^{13}$C-NMR |
| 1 | 0.7 (t) | 13.5 |
| 2 | 1.4 (m) | 18.1 or 18.5 |
| 3 | 2.0 (m) | 36.0 |
| 4 | — | 171.5 |
| 5 | 1.2 (d) | 17.8 |
| 6 | 6.7 (q) | 73.9 |
| 7 | — | 174.2 |
| 8 | 2.0 (m) | 31.0 |
| 9 | 1.4 (m) | 18.1 or 18.5 |
| 10 | 3.0 (m) | 41.9 |

$$\underset{}{\overset{10\ \ 9\ \ 8\ \ 7}{CH_2CH_2CH_2CN}}\!\!-\!\!\underset{\underset{\underset{O}{\parallel}}{\overset{4\ 3\ \ 2\ 1}{OCCH_2CH_2CH_3}}}{\overset{6\ \ 5}{CHCH_3}}$$

GC-MS analysis:
  A peak for a quasi-molecular ion M+1 corresponding to a mass number of 200 was detected by the chemical ionization method with isobutane as the reaction gas so that the molecular weight of the sample compound was 199.

IR analysis:
  1738 cm$^{-1}$ (carbonyl group at the carbon atom of position 4)
  1705 cm$^{-1}$ (carbonyl group at the carbon atom of position 7)
  1174 cm$^{-1}$ (-C-O- linkage at the carbon atom of position 4)

EXAMPLE 3

The synthetic procedure was substantially the same as in Example 1 excepting replacement of 103 g (1.2 moles) of vinyl acetate with 128 g (1 mole) of vinyl pivalate and increase of the amount of cesium hydroxide to 0.75 g (0.005 mole) to obtain 207 g of a product which could be identified to be N-(α-n-pivaloyloxyethyl)-2-pyrrolidone (97% yield of the theoretical value) from the results of the instrumental analyses shown below.

| Position of carbon atom | NMR analysis: (δ, ppm) | |
|---|---|---|
| | $^1$H-NMR | $^{13}$C-NMR |
| 1 | 1.1 (s) | 27.1 |
| 2 | — | 38.8 |
| 3 | — | 173.7 |
| 4 | 1.1 (d) | 17.7 |
| 5 | 6.8 (q) | 74.2 |
| 6 | — | 176.2 |
| 7 | 1.9 (m) | 31.0 |
| 8 | 1.3 (m) | 18.2 |
| 9 | 2.9 (m) | 41.7 |

-continued

| NMR analysis: (δ, ppm) | | |
|---|---|---|
| Position of carbon atom | ¹H-NMR | ¹³C-NMR |

```
 9   8   7  6    5  4
CH₂CH₂CH₂CN — CHCH₃
         ‖   |
         O   | 3 2 1
             OCC(CH₃)₃
             ‖
             O
```

GC-MS analysis:

A peak for a quasi-molecular ion M+1 corresponding to a mass number of 214 was detected by the chemical ionization method with isobutane as the reaction gas so that the molecular weight of the sample compound was 213.

IR analysis:

1724 cm⁻¹ (carbonyl group at the carbon atom of position 3)

1697 cm⁻¹ (carbonyl group at the carbon atom of position 6)

1155 cm⁻¹ (—C—O— linkage at the carbon atom of position 3)

EXAMPLE 4

The synthetic procedure was substantially the same as in Example 1 excepting replacement of 103 g (1.2 moles) of vinyl acetate with 148 g (1 mole) of vinyl benzoate to obtain 203 g of a product which could be identified to be N-(α-benzoyloxyethyl)-2-pyrrolidone (87% yield of the theoretical value) of the following formula from the results of the instrumental analyses shown below.

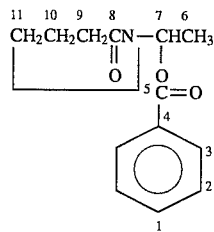

GC-MS analysis:

A peak for a quasi-molecular ion M+1 corresponding to a mass number of 234 was detected by the chemical ionization method with isobutane as the reaction gas so that the molecular weight of the sample compound was 233.

IR analysis:

1718 cm⁻¹ (carbonyl group at the carbon atom of position 5)

1664 cm⁻¹ (carbonyl group at the carbon atom of position 8)

1246 cm⁻¹ (—C—O— linkage at the carbon atom of position 5)

EXAMPLE 5

A reaction mixture was prepared by dissolving 4.5 g (0.03 mole) of cesium hydroxide in 99 g (1 mole) of δ-valerolactam under gentle warming followed by the removal of the by-product water by distillation under reduced pressure and addition of 120 ml of tetrahydrofuran. After cooling of the mixture to room temperature, 103 g (1.2 moles) of vinyl acetate were added dropwise into the reaction mixture under agitation. The conditions of the procedure otherwise were substantially the same as in Example 1 to obtain 159 g of a product which could be identified to be N-(α-acetoxyethyl)-δ-valerolactam (86% yield of the theoretical value) from the results of the instrumental analyses shown below.

| NMR analysis: (δ, ppm) | | |
|---|---|---|
| Position of carbon atom | ¹H-NMR | ¹³C-NMR |
| 1 | 1.7 (s) | 20.6 |
| 2 | — | 168.8 |
| 3 | 1.2 (d) | 17.2 |
| 4 | 7.2 (q) | 75.0 |
| 5 | — | 168.8 |
| 6 | 2.1 (t) | 32.7 |
| 7 | 1.3 (m) | 20.8 |
| 8 | 1.3 (m) | 23.0 |
| 9 | 2.9 (m) | 41.2 |

```
 9   8   7   6   5  4  3
CH₂CH₂CH₂CH₂CNCHCH₃
         ‖  ‖
         O  | 2 1
            OCCH₃
            ‖
            O
```

GC-MS analysis:

A peak for a quasi-molecular ion M+1 corresponding to a mass number of 186 was detected by the chemical ionization method with isobutane as the reaction gas so that the molecular weight of the sample compound was 185.

IR analysis:

1740 cm⁻¹ (carbonyl group at the carbon atom of position 2)

1659 cm⁻¹ (carbonyl group at the carbon atom of position 5)

1213 cm⁻¹ (—C—O— linkage at the carbon atom of position 2)

EXAMPLE 6

A reaction mixture was prepared by dissolving 2.25 g (0.015 mole) of cesium hydroxide in 113 g (1 mole) of ε-caprolactam under gentle warming followed by the removal of the by-product water by distillation under reduced pressure and addition of 150 ml of benzene. After cooling of the mixture to room temperature, this mixture was added dropwise under agitation into 120 g (1.42 moles) of vinyl acetate over a period of 15 minutes. The conditions of the procedure were otherwise substantially the same as in Example 1 to obtain 179 g of a product which could be identified to be N-(α-acetoxyethyl)-ε-caprolactam (90% yield of the theoretical value) from the results of the instrumental analyses shown below.

| NMR analysis: (δ, ppm) | | |
|---|---|---|
| Position of carbon atom | ¹H-NMR | ¹³C-NMR |
| 1 | 1.7 (s) | 20.9 |
| 2 | — | 168.6 |
| 3 | 1.1 (d) | 18.1 |
| 4 | 7.1 (q) | 75.5 |
| 5 | — | 174.6 |
| 6 | 2.3 (m) | 37.3 |

-continued

| Position of carbon atom | NMR analysis: (δ, ppm) | |
|---|---|---|
| | $^1$H-NMR | $^{13}$C-NMR |
| 7 | 1.3 (m) | 23.5 |
| 8 | 1.3 (m) | 29.8 |
| 9 | 1.3 (m) | 29.5 |
| 10 | 3.0 (m) | 42.3 |

$$\underset{10\ 9\ 8\ 7\ 6\ 5}{CH_2CH_2CH_2CH_2CH_2CH_2C}\underset{\parallel}{N}\underset{O}{-}\underset{|}{\overset{4\ 3}{CH}CH_3}$$
$$\underset{2\ 1}{OCCH_3}$$
$$\parallel$$
$$O$$

GC-MS analysis:

A peak for a quasi-molecular ion M+1 corresponding to a mass number of 200 was detected by the chemical ionization method with isobutane as the reaction gas so that the molecular weight of the sample compound was 199.

IR analysis:

1740 cm$^{-1}$ (carbonyl group at the carbon atom of position 2)

1660 cm$^{-1}$ (carbonyl group at the carbon atom of position 5)

1236 cm$^{-1}$ (—C—O— linkage at the carbon atom of position 2)

EXAMPLE 7

A reaction mixture was prepared by dissolving 3 g (0.02 mole) of cesium hydroxide in 87 g (1 mole) of 2-oxazolidone under gentle warming followed by the removal of the by-product water by distillation under reduced pressure and addition of 300 ml of tetrahydrofuran. After cooling of the mixture to room temperature, this mixture was added dropwise under agitation into 86 g (1 mole) of vinyl acetate over a period of 15 minutes. The conditions of the procedure were otherwise substantially the same as in Example 1 to obtain 139 g of a product which could be identified to be N-(α-acetoxyethyl)-2-oxazolidinone (80% yield of the theoretical value) from the results of the instrumental analyses shown below.

| Position of carbon atom | NMR analysis: (δ, ppm) | |
|---|---|---|
| | $^1$H-NMR | $^{13}$C-NMR |
| 1 | 0.7 (t) | 20.4 |
| 2 | — | 169.4 |
| 3 | 1.2 (d) | 17.9 |
| 4 | 6.4 (q) | 75.9 |
| 5 | — | 173.8 |
| 6 | 3.2 (m) | 62.6 |
| 7 | 3.9 (m) | 39.9 |

$$\underset{7\ 6}{CH_2CH_2}\underset{\parallel}{\overset{5}{O}}\underset{O}{\overset{}{C}}\underset{|}{N}\underset{2\ 1}{-\overset{4\ 3}{CH}CH_3}$$
$$OCCH_3$$
$$\parallel$$
$$O$$

GC-MS analysis:

A peak for a quasi-molecular ion M+1 corresponding to a mass number of 174 was detected by the chemical ionization method with isobutane as the reaction gas so that the molecular weight of the sample compound was 173.

IR analysis:

1765 cm$^{-1}$ (carbonyl group at the carbon atom of position 2)

1225 cm$^{-1}$ (—C—O— linkage at the carbon atom of position 2)

EXAMPLE 8

A reaction mixture was prepared by dissolving 1.03 g (0.018 mole) of potassium hydroxide in 73 g (1 mole) of N-methyl acetamide under gentle warming followed by the removal of the by-product water by distillation under reduced pressure and addition of 20 ml of benzene. After cooling of the mixture to room temperature, this mixture was added dropwise under agitation into 95 g (1.1 moles) of vinyl acetate over a period of 15 minutes. The conditions of the procedure were otherwise substantially the same as in Example 1 to obtain 132 g of a product which could be identified to be N-(α-acetoxyethyl)-N-methyl acetamide (83% yield of the theoretical value) from the results of the instrumental analyses shown below.

| Position of carbon atom | NMR analysis: (δ, ppm) |
|---|---|
| | $^1$H-NMR |
| 1 | 2.1 (s) |
| 2 | — |
| 3 | 1.1 (d) |
| 4 | 6.2 (q) |
| 5 | 2.7 (s) |
| 6 | — |
| 7 | 1.7 (m) |

$$\underset{7\ 6}{CH_3}\underset{\parallel}{\overset{\overset{5}{|}}{\underset{O}{C}}}\overset{CH_3}{-}N\underset{|}{-}\underset{2\ 1}{\overset{4\ 3}{CH}}CH_3$$
$$OCCH_3$$
$$\parallel$$
$$O$$

GC-MS analysis:

A peak for a quasi-molecular ion M+1 corresponding to a mass number of 160 was detected by the chemical ionization method with isobutane as the reaction gas so that the molecular weight of the sample compound was 159.

IR analysis:

1741 cm$^{-1}$ (carbonyl group at the carbon atom of position 2)

1649 cm$^{-1}$ (carbonyl group at the carbon atom of position 6)

1232 cm$^{-1}$ (—C—O— linkage at the carbon atom of position 2)

EXAMPLE 9

A reaction mixture was prepared by dissolving 6 g (0.04 mole) of cesium hydroxide in 87 g (1 mole) of N-ethyl acetamide under gentle warming followed by the removal of the by-product water by distillation under reduced pressure and addition of 40 ml of tetrahydrofuran. After cooling of the mixture to room temperature, this mixture was added dropwise under agitation into 86 g (1 mole) of vinyl acetate over a period of 15 minutes. The conditions of the procedure were otherwise substantially the same as in Example 1 to obtain 145 g of a product which could be identified to be N-(α-acetoxyethyl)-N-ethyl acetamide (83% yield of the theoretical value) from the results of the instrumental analyses shown below.

| NMR analysis: (δ, ppm) | |
|---|---|
| Position of carbon atom | $^1$H-NMR |
| 1 | 2.1 (s) |
| 2 | — |
| 3 | 1.1 (d) |
| 4 | 6.2 (q) |
| 5 | 3.2 (m) |
| 6 | 1.0 (t) |
| 7 | — |
| 8 | 1.7 (s) |

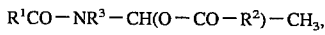

GC-MS analysis:

A peak for a quasi-molecular ion M+1 corresponding to a mass number of 174 was detected by the chemical ionization method with isobutane as the reaction gas so that the molecular weight of the sample compound was 173.

IR analysis:

1740 cm$^{-1}$ (carbonyl group at the carbon atom of position 2)

1662 cm$^{-1}$ (carbonyl group at the carbon atom of position 7)

1219 cm$^{-1}$ (—C—O— linkage at the carbon atom of position 2)

Application Example 1

Into the still of a glass-made apparatus for distillation under reduced pressure equipped with a packed distillation column and a condenser were introduced 200 g of the N-(α-acetoxyethyl)-2-pyrrolidone prepared in Example 1, which was heated therein under a reduced pressure controlled such that the thermal decomposition product was distilled out while the liquid in the still was at a temperature in the range from 80° C. to 150° C. The thus obtained distillate was subjected to distillation under reduced pressure to obtain two principal fractions, of which one was acetic acid and the other was identified to be N-vinyl-2-pyrrolidone from the results of the analyses in good coincidence with the literature values for a known compound of N-vinyl-2-pyrrolidone.

Application Example 2

The N-(α-acetoxyethyl)-2-oxazolidinone prepared in Example 7 was subjected to thermal decomposition in substantially the same manner as in Application Example 1 to obtain a distillate from which two principal fractions were obtained by distillation under reduced pressure including, one, acetic acid and, the other, N-vinyl oxazolidinone as identified from the results of the analyses in good coincidence with the literature values for a known compound of N-vinyl oxazolidinone.

Application Example 3

The N-(α-acetoxyethyl)-N-methyl acetamide prepared in Example 8 was introduced into the same apparatus as used in Application Example i and heated therein under a reduced pressure controlled such that the thermal decomposition products were distilled out while the temperature of the liquid in the still was in the range from 80° C. to 150° C. Distillation of the decomposition products was complete within 30 minutes. The distillate was, after neutralization by washing with an aqueous solution of sodium hydroxide, subjected to distillation under reduced pressure to obtain a principal fraction which could be identified to be N-vinyl-N-methyl acetamide from the results of the analyses which were in good coincidence with the literature values for a known compound of N-vinyl-N-methyl acetamide.

What is claimed is:

1. An N-(α-acyloxyethyl) compound represented by either one of the formulas

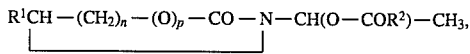

and

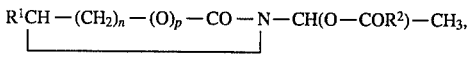

in which $R^1$ and $R^2$ are, each independently from the other, a hydrogen atom or a monovalent hydrocarbon group, $R^3$ is a monovalent hydrocarbon group, the subscript p is 0 or 1 and the subscript n is a positive integer not exceeding 10.

2. A method for the preparation of an N-(α-acyloxyethyl) compound represented by the formula

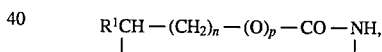

in which $R^1$ and $R^2$ are, each independently from the other, a hydrogen atom or a monovalent hydrocarbon group, the subscript p is 0 or 1 and the subscript n is a positive integer not exceeding 10, which comprises the step of: mixing an NH group-containing compound represented by the formula

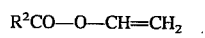

in which each symbol has the same meaning as defined above, and a vinyl carboxylate represented by the formula $$R^2CO—O—CH=CH_2.$$

in which $R^2$ has the same meaning as defined above, with admixture of an alkaline compound to effect the addition reaction between the NH group-containing compound and the vinyl carboxylate and wherein the mixture of the vinyl carboxylate and the NH group-containing compound is kept at a temperature in the range from −60° C. to 60° C.

3. The method as claimed in claim 2 in which the alkaline compound is selected from the group consisting of alkali and alkaline earth metal elements in the elementary form or in the form of a hydroxide, carbonate, hydrogencarbonate, hydrogenphosphate, acetate or alcoholate.

4. The method as claimed in claim 2 in which the amount of the alkaline compound is in the range from 0.0001 to 0.2 mole per mole of the NH group-containing compound.

5. The method as claimed in claim 2 in which the amount of the vinyl carboxylate is in the range from 1 to 2 moles per mole of the NH group-containing compound.

6. A method for the preparation of an N-(α-acyloxyethyl) compound represented by the formula $R^1CO-NR^3-CH-(O-CO-R^2)-CH_3$ in which $R^1$ and $R^2$ are, each independently from the other, a hydrogen atom or a monovalent hydrocarbon group and $R^3$ is a monovalent hydrocarbon group, which comprises the step of: mixing an NH group-containing compound represented by the formula $R^1CO-NHR^3$, in which each symbol has the same meaning as defined and a vinyl carboxylate represented by the formula $R^2-CO-O-CH=CH_2$ in which $R^2$ has the same meaning as defined above, with admixture of an alkaline compound to effect the addition reaction between the NH group-containing compound and the vinyl carboxylate and wherein the mixture of the vinyl carboxylate and the NH group-containing compound is kept at a temperature in the range from −60° C. to 60° C.

7. The method as claimed in claim 3 in which the alkaline compound is an alkali metal hydroxide.

8. The method as claimed in claim 7 in which the alkali metal hydroxide is dissolved in the NH group-containing compound to form a mixture containing water as a by-product of the reaction between the alkali metal hydroxide and the NH group-containing compound and the by-product water is removed before the mixture is further mixed with the vinyl carboxylate.

9. The method as claimed in claim 6 in which the alkaline compound is selected from the group consisting of alkali and alkaline earth metal elements in the elementary form or in the form of a hydroxide, carbonate, hydrogencarbonate, hydrogenphosphate, acetate or alcoholate.

10. The method as claimed in claim 6 in which the amount of the alkaline compound is in the range from 0.0001 to 0.2 mole per mole of the NH group-containing compound.

11. The method as claimed in claim 5 in which the amount of the vinyl carboxylate is in the range from 1 to 2 moles per mole of the NH group-containing compound.

12. The method as claimed in claim 6 in which the alkaline compound is an alkali metal hydroxide.

13. The method as claimed in claim 12 in which the alkali metal hydroxide is dissolved in the NH groups-containing compound to form a mixture containing water as a by-product of the reaction between the alkali metal hydroxide and the NH group-containing compound and the by-product water is removed before the mixture is further mixed with the vinyl carboxylate.

* * * * *